(12) United States Patent
Greenberg

(10) Patent No.: US 8,945,205 B2
(45) Date of Patent: Feb. 3, 2015

(54) BRANCH VESSEL PROSTHESES

(75) Inventor: Roy K. Greenberg, Bratenahl, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/449,923

(22) Filed: Apr. 18, 2012

(65) Prior Publication Data

US 2013/0041456 A1 Feb. 14, 2013

Related U.S. Application Data

(60) Provisional application No. 61/480,104, filed on Apr. 28, 2011.

(51) Int. Cl.
*A61F 2/06* (2013.01)
*A61F 2/07* (2013.01)
*A61F 2/89* (2013.01)

(52) U.S. Cl.
CPC . *A61F 2/07* (2013.01); *A61F 2/064* (2013.01); *A61F 2002/061* (2013.01); *A61F 2002/067* (2013.01); *A61F 2250/0039* (2013.01); *A61F 2250/006* (2013.01); *A61F 2250/0069* (2013.01); *A61F 2/89* (2013.01); *A61F 2002/075* (2013.01)
USPC .......................................... 623/1.35; 623/1.1

(58) Field of Classification Search
CPC ............. A61F 2/06; A61F 2/07; A61F 2/954; A61F 2/856
USPC ......................................................... 623/1.35
See application file for complete search history.

(56) References Cited

U.S. PATENT DOCUMENTS

| | | | |
|---|---|---|---|
| 6,645,242 B1 * | 11/2003 | Quinn | 623/1.16 |
| 7,105,020 B2 | 9/2006 | Greenberg et al. | |
| 7,976,575 B2 * | 7/2011 | Hartley | 623/1.11 |
| 2002/0156521 A1 * | 10/2002 | Ryan et al. | 623/1.13 |
| 2006/0184228 A1 | 8/2006 | Khoury | |

(Continued)

FOREIGN PATENT DOCUMENTS

| | | |
|---|---|---|
| WO | WO03/082153 | 10/2003 |
| WO | WO2006/113501 | 10/2006 |
| WO | WO2008/073964 | 6/2008 |

OTHER PUBLICATIONS

Partial European Search Report for EP12275053 dated Nov. 19, 2012, 10 pgs.

(Continued)

*Primary Examiner* — Thomas J Sweet
*Assistant Examiner* — Tiffany Shipmon
(74) *Attorney, Agent, or Firm* — Brinks Gilson & Lione

(57) ABSTRACT

The present embodiments provide a branch vessel prosthesis for placement at least partially between a main vessel and a branch vessel of a patient. The branch vessel prosthesis has a graft including a generally tubular body of a biocompatible material. At least one stent is coupled to a proximal region of the graft, and at least one stent is coupled to a distal region of the graft. The proximal region of the graft includes a generally straight configuration in an expanded deployed state that is substantially parallel to a longitudinal axis of a main vessel. The distal region of the graft includes a generally straight configuration in the expanded deployed state that is substantially parallel to a branch vessel. A curvature of a central region varies an angle in which the distal region of the graft is disposed relative to the proximal region.

20 Claims, 2 Drawing Sheets

(56) References Cited

U.S. PATENT DOCUMENTS

2006/0247761 A1* 11/2006 Greenberg et al. .......... 623/1.16
2007/0219621 A1 9/2007 Hartley et al.
2008/0109066 A1 5/2008 Quinn

OTHER PUBLICATIONS

Examination Report for EP 12 275 053.2 dated Aug. 8, 2013, 5 pgs.
Response to Examination Report for EP 12 275 053.2 dated Dec. 16, 2013, 15 pgs.

* cited by examiner

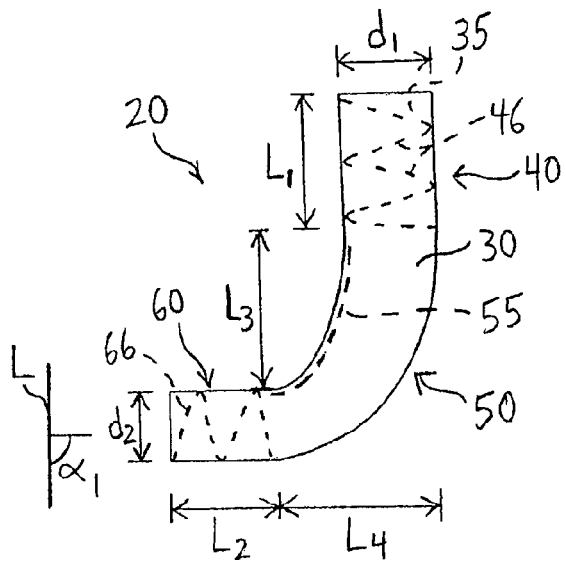
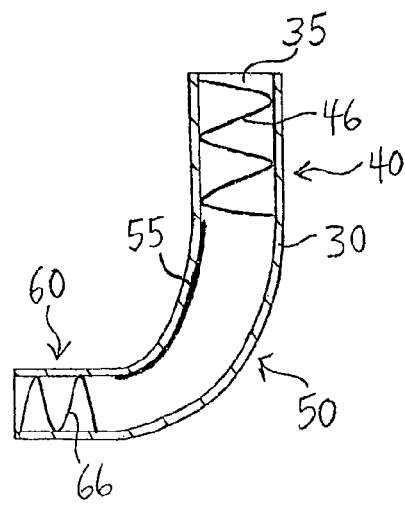
FIG. 1A  FIG. 1B
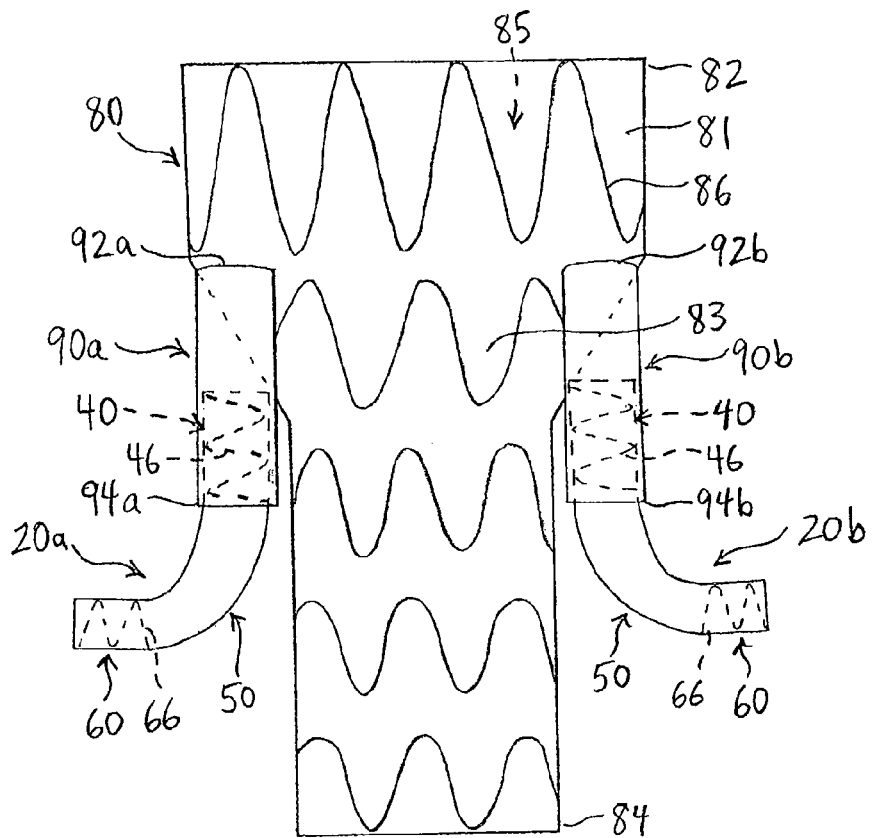
FIG. 2

BRANCH VESSEL PROSTHESES

PRIORITY CLAIM

This invention claims the benefit of priority of U.S. Provisional Application Ser. No. 61/480,104, entitled "Branch Vessel Prostheses," filed Apr. 28, 2011, the disclosure of which is hereby incorporated by reference in its entirety.

BACKGROUND

The present embodiments relate generally to medical devises, and more particularly, to branch vessel prostheses that may be used with a main vessel prosthesis.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. In Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurysmal or ruptured vessels involves the use of an endoluminal prosthesis to provide some or all of the functionality of the original, healthy vessel and/or preserve any remaining vascular integrity by replacing a length of the existing vessel wall that spans the site of vessel failure. These prostheses may seal off the failed portion of the vessel. For weakened or aneurysmal vessels, even a small leak in the prosthesis may lead to the pressurization of or flow in the treated vessel, which aggravates the condition the prosthesis was intended to treat. A prosthesis of this type can, for example, treat aneurysms of the abdominal aortic, iliac, or branch vessels such as the renal arteries.

An endoluminal prosthesis can be of a unitary construction, or be comprised of multiple prosthetic modules. A modular prosthesis allows a surgeon to accommodate a wide variation in vessel morphology while reducing the necessary inventory of differently sized prostheses. For example, aortas vary in length, diameter and angulation between the renal artery region and the region of the aortic bifurcation. Prosthetic modules that fit each of these variables can be assembled to form a prosthesis, obviating the need for a custom prosthesis or large inventories of prostheses that accommodate all possible combinations of these variables. A modular system may also accommodate deployment options by allowing the proper placement of one module before the implantation of an adjoining module.

Modular systems are typically assembled in situ by overlapping the tubular ends of the prosthetic modules so that the end of one module sits partially inside the other module, preferably forming circumferential apposition through the overlap region. This attachment process is called "tromboning." The connections between prosthetic modules are typically maintained by the friction forces at the overlap region and enhanced by the radial force exerted by the internal prosthetic module on the external prosthetic modules where the two overlap.

When an aneurysm affects a main vessel, it is important to maintain flow to the branch vessels. The celiac, superior mesenteric, left common carotid and renal arteries, for example, are branch vessels of the aorta; the hypogastric artery is a branch vessel of the common iliac artery. If these branch vessels are blocked by the main vessel prosthesis, the original blood circulation is impeded, and the patient can suffer. If, for example, the celiac artery is blocked by the main vessel prosthesis, the patient can experience abdominal pain, weight loss, nausea, bloating and loose stools associated with mesenteric ischemia. The blockage of any branch vessel is usually associated with unpleasant or even life-threatening symptoms.

SUMMARY

The present embodiments provide a branch vessel prosthesis for placement at least partially between a main vessel and a branch vessel of a patient. The branch vessel prosthesis comprises a graft including a generally tubular body of a biocompatible material, and has proximal and distal regions, a central region disposed between the proximal and distal regions, and a lumen extending between the proximal and distal regions. At least one stent is coupled to the proximal region of the graft, and at least one stent is coupled to the distal region of the graft. The proximal region of the graft includes a generally straight configuration in an expanded deployed state that is substantially parallel to a longitudinal axis of a main vessel. The distal region of the graft includes a generally straight configuration in the expanded deployed state that is substantially parallel to a branch vessel. A curvature of the central region varies an angle in which the distal region of the graft is disposed relative to the proximal region.

In one embodiment, an outer diameter at the proximal region of the graft is greater than an outer diameter at the distal region of the graft in the expanded deployed state. In one embodiment, a longitudinal length of the proximal region of the graft is greater than a longitudinal length of the distal region of the graft in the expanded deployed state. In another example, the central region comprises at least one cross-sectional area that is greater than a cross-sectional area of each of proximal and distal regions. An expansion member optionally may be coupled to the central region to promote a curvature of the central region in the expanded deployed state.

In one example, the angle in which the distal region of the graft is disposed relative to the proximal region of the graft is between about 80 degrees and about 100 degrees. In alternative examples, the angle in which the distal region of the graft is disposed relative to the proximal region of the graft is between about 20 degrees and about 40 degrees, or between about 110 degrees and about 130 degrees.

The branch vessel prosthesis may be configured for use with a main vessel prosthesis comprising a graft including a generally tubular body of a biocompatible material and having proximal and distal ends and a lumen extending therebetween. At least a first branch extends longitudinally from the graft of the main vessel prosthesis. The proximal region of the branch vessel prosthesis is adapted to be disposed in an overlapping relation within the first branch of the main vessel prosthesis in the expanded deployed state.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention.

Moreover, in the figures, like referenced numerals designate corresponding parts throughout the different views.

FIGS. 1A-1B are side and side-sectional views, respectively, of a branch vessel prosthesis according to a first embodiment in an expanded deployed state.

FIG. 2 is a side view of a main vessel prosthesis coupled to the branch vessel prosthesis of FIGS. 1A-1B.

DETAILED DESCRIPTION OF THE PREFERRED EMBODIMENTS

Figure 3:
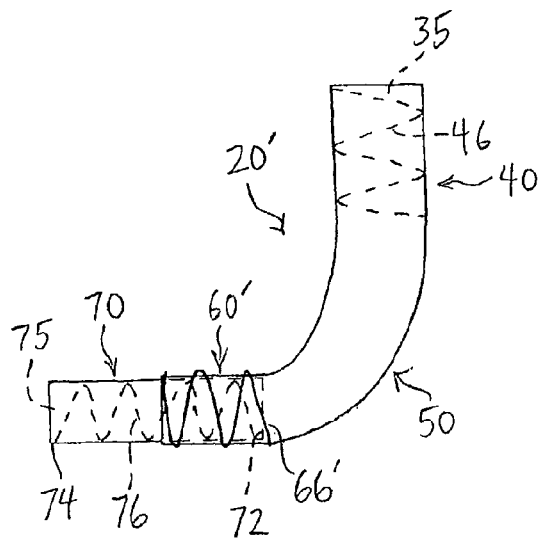
FIG. 3 is a side view of an alternative branch vessel prosthesis coupled to a branch extension prosthesis in an expanded deployed state.

In the present application, the term "proximal" refers to a direction that is generally closest to the heart during a medical procedure, while the term "distal" refers to a direction that is furthest from the heart during a medical procedure.

Referring now to FIGS. 1A-1B, a first embodiment of a branch vessel prosthesis 20 is shown and described. The branch vessel prosthesis 20 comprises a graft 30 including a generally tubular body of a biocompatible material. In this embodiment, the branch vessel prosthesis 20 comprises a proximal region 40, a distal region 60, and a central region 50 disposed between the proximal and distal regions 40 and 60. A lumen 35 allows fluid flow between the proximal and distal regions 40 and 60 in the expanded deployed state shown in FIGS. 1A-1B.

Many different types of graft materials may be used for the graft 30. Common examples of graft materials currently used include expandable polytetrafluoroethylene (ePTFE), polytetrafluoroethylene (PTFE), Dacron, polyester, fabrics and collagen. However, graft materials may be made from numerous other materials as well, including both synthetic polymers and natural tissues.

In the embodiment of FIGS. 1A-1B, the proximal region 40 of the graft 30 includes a generally straight configuration in the expanded deployed state that is substantially parallel to a longitudinal axis L, and the distal region 60 of the graft 30 includes a generally straight configuration that is substantially parallel to a branch vessel. A curvature of the central region 50 varies a first angle $\alpha_1$ in which the distal region 60 of the graft 30 is disposed relative to the proximal region 40 of the graft 30.

The proximal region 40 is configured to be modularly coupled to a first branch 90a of a main vessel prosthesis 80, as depicted in FIG. 2. In one exemplary embodiment described with respect to FIG. 2, the main vessel is a patient's abdominal aorta, while the branch vessels are the left and right renal arteries. However, various alternative locations are possible, some of which are described below in non-limiting examples.

In the examples herein, the first branch 90a of the main vessel prosthesis 80 extends generally parallel to a main vessel, such as the abdominal aorta. Thus, when the proximal region 40 of the branch vessel prosthesis 20 is deployed in the generally straight configuration and overlaps with the first branch 90a as shown in FIG. 2, the proximal region 40 is also oriented generally parallel to the main vessel. The curved region 50 allows the distal region 60 of the branch vessel prosthesis 20 to conform to the pertinent branch vessel anatomy.

In one example, if the branch vessel, such as a renal artery, is disposed at an angle of about 80-100 degrees relative to a main vessel, such as the abdominal aorta, then the curvature of the central region 50 allows the proximal and distal regions 40 and 60 to be disposed at a corresponding first angle $\alpha_1$ of between about 80-110 degrees to provide a curved transition for fluid flow from the main vessel in a direction towards the branch vessel. While the first angle $\alpha_1$ is between about 80-100 degrees in the example of FIG. 1, the angle may be greater or less, as described for example in the embodiment of FIGS. 4-5 below.

The distal region 60 of the branch vessel prosthesis 20 may extend directly into the branch vessel and may engage an inner wall of the branch vessel. Optionally, an extension prosthesis 70 may be coupled to the branch vessel prosthesis 20 to extend from the branch vessel prosthesis 20 into engagement with the branch vessel, as explained further in FIG. 3 below.

At least one stent 46 is coupled to the proximal region 40 of the graft 30, and at least one stent 66 is coupled to the distal region 60 of the graft 30. In the embodiment of FIGS. 1A-1B, a single stent 46 is coupled to an interior surface of the proximal region 40 of the graft 30, and a single stent 66 is coupled to an interior surface of the distal region 60 of the graft 30. The stent 46 may be coupled to the interior surface of the proximal region 40 to provide a smooth outer surface along the proximal region 40 that promotes a relatively flush overlapping engagement with the first branch 90a, as shown in FIG. 2. While one exemplary arrangement is shown in FIGS. 1A-1B, it will be appreciated that the exact number of stents, and their location, may be varied.

The stents 46 and 66 may be made from numerous metals and alloys. In one example, the stents 46 and 66 comprise a shape-memory material such as a nickel-titanium alloy ("nitinol"). Moreover, the structure of the stents 46 and 66 may be formed in a variety of ways to provide a suitable intraluminal support structure. For example, one or more stents may be made from a woven wire structure, a laser-cut cannula, individual interconnected rings, or another pattern or design.

In one example, shown in FIGS. 1A-1B, the stents 46 and 66 may be configured in the form of one or more "Z-stents" or Gianturco stents, each of which may comprise a series of substantially straight segments interconnected by a series of bent segments. The bent segments may comprise acute bends or apices. The Gianturco stents are arranged in a zigzag configuration in which the straight segments are set at angles relative to each other and are connected by the bent segments. However, as noted above, the stents 46 and 66 may comprise any suitable configuration and one or more stents may be provided.

Optionally, an expansion member 55 may be coupled to the central region 50 of the graft 30. The expansion member 55 may promote an intended curvature of the central region 50 in the expanded deployed state shown in FIGS. 1A-1B. The expansion member 55 may be coupled to an interior or exterior surface of the graft 30. By way of example, and without limitation, the expansion member 55 may comprise a wire, coil, or other suitable member, and may be made from a resilient pre-formed material such as plastic, shape-memory alloys, stainless steel, and the like. Alternatively, the expansion member 55 may be omitted and, with the proximal and distal regions 40 and 60 being stented for patency in the expanded deployed state, blood flow alone may maintain patency within the lumen 35 along the central region 50 of the graft 30.

In one example, an outer diameter $d_1$ at the proximal region 40 of the graft 30 may be greater than an outer diameter $d_2$ at the distal region 60 of the graft 30 in the expanded deployed state, as depicted in FIGS. 1A-1B. The provision of an increased outer diameter $d_1$ at the proximal region 40 of the graft 30 may promote an enhanced frictional coupling to an inner surface of the first branch 90a, as shown in FIG. 2. If the outer diameter $d_1$ is greater than the outer diameter $d_2$, the diameter of the graft 30 may taper in a relatively uniform manner along the central region 50 to accommodate the change in outer diameter. In alternative embodiments, the outer diameters $d_1$ and $d_2$ may be about the same, or the outer diameter $d_2$ may be greater than the outer diameter $d_1$, depending on factors such as the anatomy of the patient.

Moreover, a longitudinal length $L_1$ of the proximal region 40 of the graft 30 may be greater than a longitudinal length $L_2$ of the distal region 60 of the graft 30 in the expanded deployed state, as depicted in FIGS. 1A-1B. The provision of an increased longitudinal length $L_1$ of the proximal region 40 may promote an enhanced frictional coupling to an inner surface of the first branch 90a, as shown in FIG. 2. Additionally, if the proximal region 40 comprises a greater axial length, then a longer stent 46, or multiple stents, may be provided for an enhanced coupling. In alternative embodiments, the longitudinal lengths $L_1$ and $L_2$ may be about the same, or the longitudinal length $L_2$ may be greater than the longitudinal length $L_1$, depending on factors such as the anatomy of the patient.

The central region 50 curves and ultimately covers a longitudinal length $L_3$ and a lateral length $L_4$, which are functions of the curvature and distance of the central region 50. In one example, the longitudinal length $L_3$ is greater than 3 cm, which may assist in transitioning fluid flowing through a main vessel towards a branch vessel at a given angle.

Referring to FIG. 2, further features of an exemplary main vessel prosthesis 80, compatible for use with the branch vessel prosthesis 20 of FIGS. 1A-1B, are shown and described. The main vessel prosthesis 80 comprises a graft 81 including a generally tubular body of a biocompatible material and having proximal and distal ends 82 and 84 and a lumen 85 extending therebetween. In the example of FIG. 2, the main vessel prosthesis 80 comprises first and second branches 90a and 90b. The first branch 90 has proximal and distal ends 92a and 94a and a lumen extending therebetween. In one example, at least one or both of the first and second branches 90a and 90b extends in a generally straight manner along the longitudinal axis L. A wall of the graft 81 may have fenestration formed therein, and the proximal end 92a of the first branch 90a may be anastamosed to the graft 80 in a manner to provide fluid flow from the lumen 85 of the main vessel prosthesis 80 into the lumen of the first branch 90a. Similarly, another fenestration may be formed in the graft 81, such that the proximal end 92b of the second branch 90b may be anastamosed to the graft 80 to provide fluid flow from the lumen 85 of the main vessel prosthesis 80 into the lumen of the second branch 90b.

In the embodiment of FIG. 2, the main vessel prosthesis 80 has a tapered portion 83 that decreases an outer diameter of the tubular body in a proximal to distal longitudinal direction, such that an outer diameter at the proximal end 82 is greater than an outer diameter at the distal end 84 of the graft 81. In the exemplary embodiment of FIG. 2, the proximal ends 92a and 92b of the first and second branches 90a and 90b, respectively, are disposed within the tapered portion 83. Alternatively, the proximal ends 92a and 92b of the first and second branches 90a and 90b may be disposed in any of the proximal, tapered and/or distal regions of the main vessel prosthesis 80.

The first and second branches 90a and 90b may be disposed around a circumference of the graft 80 at a predetermined distance relative to one another. In the example of FIG. 2, the first and second branches 90a and 90b are disposed about 180 degrees apart relative to one another. In various alternative embodiments, the first and second branches 90a and 90b may be disposed closer or further from one another, and fewer or greater than two branches may be used as part of the main vessel prosthesis.

In one example, the main vessel prosthesis 80 may be configured to be positioned within the aorta so that first and second branch vessel prostheses 20a and 20b, when coupled to the first and second branches 90a and 90b, respectively, can extend into the renal arteries. However, the modular prosthesis design can be adapted for use in other vessels as noted herein.

The main vessel prosthesis 80 has a compressed, reduced diameter delivery state in which it may be advanced to a target location within a vessel, duct or other anatomical site, such as the abdominal aorta. One or more radiopaque markers may be provided to provide radiographic visualization of the position of the main vessel prosthesis 80 and the branch vessel prostheses 20a and 20b when placed in the vessel or duct of a patient. A plurality of radiopaque markers may be coupled to the main vessel prosthesis 80 and/or the branch vessel prostheses 20a and 20b to facilitate imaging of various desired locations along the length of the endoluminal prostheses shown herein.

The main vessel prosthesis 80 further has an expanded state, as shown in FIG. 2, in which it may be configured to apply a radially outward force upon the vessel, duct or other target location. In the expanded state, fluid flow is allowed through the lumen 85 of the graft 81. One or more stents 86 may be coupled to interior and/or exterior surfaces of the graft 81 to maintain patency in the expanded state. Optionally, one or more uncovered stents may be provided for suprarenal fixation of the main vessel prosthesis 80 and may comprise barbs for engaging a tissue segment in the expanded state.

In an exemplary method step for using the main vessel prosthesis 80 of FIG. 2 to treat a condition in the area of a patient's abdominal aorta, the main vessel prosthesis 80 is compressed into a delivery state, and is delivered into the patient's abdominal aorta using a suitable deployment system or introducer. An introducer, such as that described in PCT application WO98/53761, entitled "A Prosthesis and a Method and Means of Deploying a Prosthesis," which is incorporated herein by reference in its entirety, may be used to deploy the main vessel prosthesis 80. PCT application WO98/53761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath.

In one exemplary technique, the branch vessel prostheses 20a and 20b then are delivered in compressed states in a proximal to distal direction into the first and second branches 90a and 90b, respectively. The branch vessel prostheses 20a and 20b may be delivered in compressed states using a wire guide and delivery catheter that are advanced through a patient's brachial artery and towards the main vessel prosthesis 80 in a proximal to distal direction. The delivery catheter housing the branch vessel prostheses 20a is advanced distally within the lumen 85 of the main vessel prosthesis 80, then into the lumen of the first branch 90a in a direction from the proximal end 92a towards the distal region 94a. The wire guide may be inserted into the branch vessel, such as the renal arteries, at this time. The branch vessel prosthesis 20a is positioned relative to the main vessel prosthesis 80 such that the proximal region 40 of the branch vessel prosthesis 20a overlaps with the first branch 90a of the main vessel prosthesis 80 a sufficient distance. Additionally, the distal region 60 of the branch vessel prosthesis 20a may overlap with the branch vessel a sufficient distance.

The delivery catheter then may be retracted relative to the branch vessel prostheses 20a to allow the proximal and distal regions 40 and 60 of the branch vessel prosthesis 20a to self-expand into a secure, frictional, tromboning engagement with the first branch 90a and the branch vessel, respectively. An overlap of about 1.5 to 2 cm, and a 1 mm or less difference in diameter, is desirable at the interconnection between the proximal region 40 and the first branch 90a. Alternatively, or in addition to self-expansion, the branch vessel prosthesis 20a may be balloon-expanded into engagement with the first branch 90a and the branch vessel. After deployment of the branch vessel prosthesis 20a, the branch vessel prosthesis 20b then may be delivered and deployed into engagement with the second branch 90b and another branch vessel in the manner described above for the branch vessel prosthesis 20a, resulting in the modular structure shown in FIG. 2.

Referring now to FIG. 3, a branch extension prosthesis 70 may be coupled to a distal region 60' of an alternative branch vessel prosthesis 20', thereby extending from the branch vessel prosthesis 20' into engagement with the branch vessel. In one embodiment, an outer surface of the distal region 60' of the branch vessel prosthesis 20' engages an inner wall of the branch vessel, and the branch extension prosthesis 70 extends further into the branch vessel distally for a more secure engagement with the branch vessel. In this example, one or more stents 66' preferably is coupled to an exterior surface of the distal region 60' to promote a flush overlapping engagement between the branch vessel prosthesis 20' and the branch extension prosthesis 70.

In the example of FIG. 3, the branch extension prosthesis 70 comprises proximal and distal ends 72 and 74 and a lumen 75 extending therebetween to maintain fluid flow from the branch vessel prosthesis 20' into the branch vessel. At least one stent 76, such as one or more z-shaped stents, is secured to the branch extension prosthesis 70. The stent 76 may be coupled to the interior surface of the branch extension prosthesis 70 to provide a smooth outer surface that promotes a flush overlapping engagement with the distal region 60' of the branch vessel prosthesis 20', as shown in FIG. 3. Optionally, stent 76 may extend distally beyond to the distal end 74 of the branch extension prosthesis 70 and may directly engage the inner wall of the branch vessel.

In an alternative embodiment, the distal region 60' of the branch vessel prosthesis 20' and the branch extension prosthesis 70 may comprise complementary annular crimps. Complementary crimping or other types of projections at the tromboning interconnection may help maintain a sealing overlapping relationship and prevent pull-out. Such complementary annular crimps also may be provided at the overlapping interface between the proximal region 40 of the branch vessel prosthesis 20 and the respective branch of the main vessel prosthesis 80.

Figure 4:
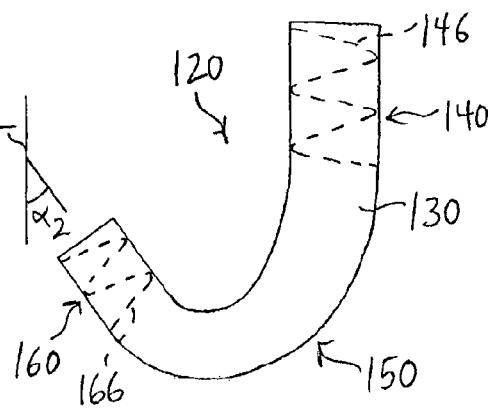
FIG. 4 is a side view of a further alternative branch vessel prosthesis in an expanded deployed state.

Referring now to FIG. 4, an alternative branch vessel prosthesis 120 is shown and described. The alternative branch vessel prosthesis 120 is similar to the branch vessel prosthesis 20 of FIGS. 1A-1B, with a main exception that a second angle $\alpha_2$ in which a distal region 160 of a graft 130 is disposed relative to a proximal region 140 of the graft 130 is more acute than the first angle $\alpha_1$ in FIGS. 1A-1B. In this non-limiting example, the distal region 160 of the graft is disposed at the second angle $\alpha_2$ that is between about 20 degrees and about 40 degrees relative to the proximal region 140 of the graft 130. The alternative branch vessel prosthesis 120 may be suitable for branch vessels that are disposed at such a second angle $\alpha_2$ relative to the main vessel. The longitudinal lengths of the proximal and distal regions 140 and 160, as well as the stents 146 and 166, may be provided in accordance with the corresponding lengths and stents described in FIGS. 1A-1B above. An optional expansion member may be coupled to the central region 150 of the graft 130, in a manner similar to the expansion member 55 of FIGS. 1A-1B, to promote an intended curvature of the central region 150 in the expanded deployed state shown in FIG. 4.

Figure 5:
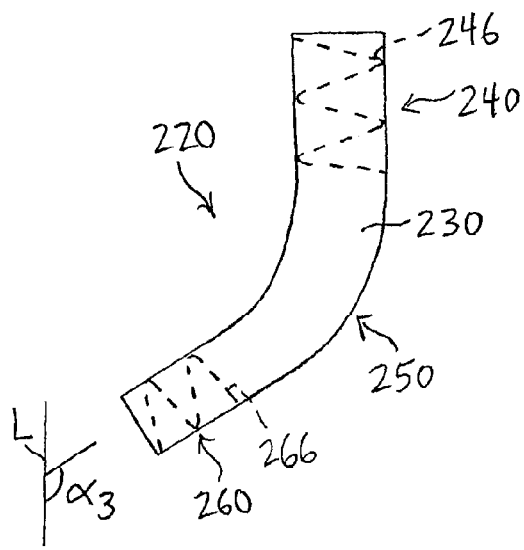
FIG. 5 is a side view of still a further alternative branch vessel prosthesis in an expanded deployed state.

Referring now to FIG. 5, an alternative branch vessel prosthesis 220 is shown and described. The alternative branch vessel prosthesis 220 is similar to the branch vessel prosthesis 20 of FIGS. 1A-1B, with a main exception that a third angle $\alpha_3$ in which a distal region 260 of a graft 230 is disposed relative to a proximal region 240 of the graft 230 is more obtuse than the first angle $\alpha_1$ in FIGS. 1A-1B. In this non-limiting example, the distal region 260 of the graft 230 is disposed at the third angle $\alpha_3$ that is between about 110 degrees and about 130 degrees relative to the proximal region 240 of the graft 230. The alternative branch vessel prosthesis 220 may be suitable for branch vessels that are disposed at such a third angle $\alpha_3$ relative to the main vessel. As in the previous embodiments, the longitudinal lengths of the proximal and distal regions 240 and 260, as well as stents 246 and 266, may be provided in accordance with FIGS. 1A-1B above. An optional expansion member may be coupled to the central region 250 of the graft 230, in a manner similar to the expansion member 55 of FIGS. 1A-1B, to promote an intended curvature of the central region 250 in the expanded deployed state shown in FIG. 5.

Figure 6:
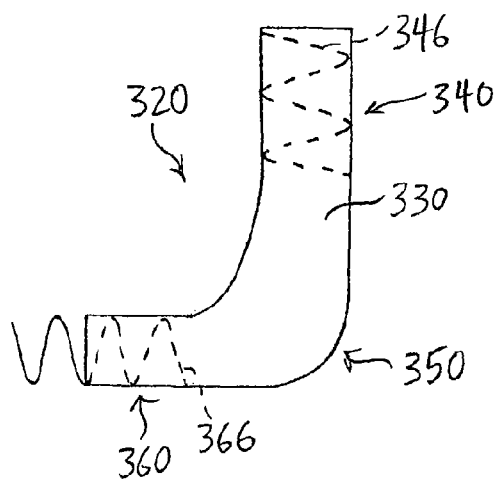
FIG. 6 is a side view of yet a further alternative branch vessel prosthesis in an expanded deployed state.

Referring now to FIG. 6, an alternative branch vessel prosthesis 320 is shown and described. The alternative branch vessel prosthesis 320 is similar to the branch vessel prosthesis 20 of FIGS. 1A-1B, with a main exception that a wider central region 350 is provided. In the example of FIG. 6, the central region 350 comprises at least one cross-sectional area that is greater than a cross-sectional area of each of proximal and distal regions 340 and 360. Moreover, while a stent 346 of the proximal region 340 may be provided in accordance with the stent 46 of FIGS. 1A-1B, in the embodiment of FIG. 6 a stent 366 of the distal region 360 extends distally beyond a distal end of the distal region 360 such that an exposed portion of the stent 366 may directly engage an inner wall of the branch vessel.

It will be appreciated that the exact number, orientation, and placement of the various branch vessel prostheses 20, 20', 120, 220 and 320, along the main vessel prosthesis 80, may be varied without departing from the spirit of the present embodiments. Moreover, while one exemplary procedure has been described with reference to the abdominal aorta and its branches, a main vessel prosthesis having multiple branches as described herein may be used in other procedures.

For example, in an embodiment where the main vessel prosthesis 80 is deployed so that the body 81 is placed at least partially in the abdominal aorta, the various branch vessel prostheses 20, 20', 120, 220 and 320 may shunt blood flow to a celiac, superior mesenteric, left subclavian, common carotid, innominate, a first renal artery, first and second renal arteries, or any suitable combination of the above listed branch vessels.

Alternatively, in an embodiment where the main vessel prosthesis 80 is deployed so that the body 81 is placed at least partially in the common iliac, the various branch vessel prostheses 20, 20', 120, 220 and 320 may shunt blood flow to a hypogastric artery. In a still further alternative in which the main vessel prosthesis 80 is deployed so that the body 81 is placed at least partially in the thoracic aorta, the various branch vessel prostheses 20, 20', 120, 220 and 320 may shunt blood flow to the innominate, left common carotid or left subclavian artery. Moreover, any of the stents mentioned herein may have barbs to help decrease prosthesis migration in any of the foregoing examples.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A branch vessel prosthesis for placement at least partially between a main vessel and a branch vessel of a patient, the branch vessel prosthesis comprising:
    a graft including a generally tubular body of a biocompatible material, the graft having proximal and distal regions, a central region disposed between the proximal and distal regions, and a lumen extending between the proximal and distal regions;
    at least one stent coupled to the proximal region of the graft, where the proximal region of the graft includes a generally straight configuration in an expanded deployed state that is substantially parallel to a longitudinal axis of a main vessel; and
    at least one stent coupled to the distal region of the graft, where the distal region of the graft includes a generally straight configuration in the expanded deployed state that is substantially parallel to a branch vessel,
    where a curvature of the central region varies an angle in which the distal region of the graft is disposed relative to the proximal region of the graft, and
    where an outer diameter at the proximal region of the graft is greater than an outer diameter at the distal region of the graft in the expanded deployed state, and where the proximal region of the branch vessel prosthesis is disposed within a main vessel prosthesis.

2. The branch vessel prosthesis of claim 1, where a longitudinal length of the proximal region of the graft is greater than a longitudinal length of the distal region of the graft in the expanded deployed state.

3. The branch vessel prosthesis of claim 1 further comprising an expansion member coupled to the central region, where the expansion member promotes a curvature of the central region in the expanded deployed state.

4. The branch vessel prosthesis of claim 1, where the central region comprises at least one cross-sectional area that is greater than a cross-sectional area of each of the proximal and distal regions.

5. The branch vessel prosthesis of claim 1, where the angle in which the distal region of the graft is disposed relative to the proximal region of the graft is between about 80 degrees and about 100 degrees.

6. The branch vessel prosthesis of claim 1, where the angle in which the distal region of the graft is disposed relative to the proximal region of the graft is between about 20 degrees and about 40 degrees.

7. The branch vessel prosthesis of claim 1, where the angle in which the distal region of the graft is disposed relative to the proximal region of the graft is between about 110 degrees and about 130 degrees.

8. The branch vessel prosthesis of claim 1, where the at least one stent coupled to the proximal region of the graft is disposed internal to the graft, and where the at least one stent coupled to the distal region of the graft is disposed external to the graft.

9. The branch vessel prosthesis of claim 1, wherein a branch extension prosthesis is configured to be disposed in a frictional overlapping relationship with the distal region of the branch vessel prosthesis.

10. The branch vessel prosthesis of claim 1, where the main vessel prosthesis comprises a graft including a generally tubular body of a biocompatible material and having proximal and distal ends and a lumen extending therebetween, where at least a first branch extends longitudinally from the graft of the main vessel prosthesis.

11. The branch vessel prosthesis of claim 10, where the graft of the main vessel prosthesis comprises a tapered portion that decreases an outer diameter of the tubular body of the main vessel prosthesis in a proximal to distal longitudinal direction, where a proximal end of the first branch is anastomosed to the tapered portion.

12. A branch vessel prosthesis for placement at least partially between a main vessel and a branch vessel of a patient, the prosthesis comprising:
    a graft including a generally tubular body of a biocompatible material, the graft having proximal and distal regions, a central region disposed between the proximal and distal regions, and a lumen extending between the proximal and distal regions;
    at least one stent coupled to the proximal region of the graft, where the proximal region of the graft includes a generally straight configuration in an expanded deployed state that is substantially parallel to a longitudinal axis of a main vessel; and
    at least one stent coupled to the distal region of the graft, where the distal region of the graft includes a generally straight configuration in the expanded deployed state that is substantially parallel to a branch vessel,
    where a curvature of the central region varies an angle in which the distal region of the graft is disposed relative to the proximal region of the graft, and
    where a longitudinal length of the proximal region of the graft is greater than a longitudinal length of the distal region of the graft in the expanded deployed state.

13. The branch vessel prosthesis of claim 12, where an outer diameter at the proximal region of the graft is greater than an outer diameter at the distal region of the graft in the expanded deployed state.

14. The branch vessel prosthesis of claim 12 further comprising an expansion member coupled to the central region, where the expansion member promotes a curvature of the central region in the expanded deployed state.

15. The branch vessel prosthesis of claim 12, where the central region comprises at least one cross-sectional area that is greater than a cross-sectional area of each of proximal and distal regions.

16. The branch vessel prosthesis of claim 12, where the branch vessel prosthesis is configured for use with a main vessel prosthesis comprising a graft including a generally tubular body of a biocompatible material and having proximal and distal ends and a lumen extending therebetween, where at least a first branch extends longitudinally from the graft of the main vessel prosthesis, and where the proximal region of the branch vessel prosthesis is adapted to be disposed in an overlapping relation within at least a portion of the first branch of the main vessel prosthesis in the expanded deployed state.

17. A branch vessel prosthesis for placement at least partially between a main vessel and a branch vessel of a patient, the branch vessel prosthesis comprising:

a graft including a generally tubular body of a biocompatible material, the graft having proximal and distal regions, a central region disposed between the proximal and distal regions, and a lumen extending between the proximal and distal regions;

at least one stent coupled to the proximal region of the graft, where the proximal region of the graft includes a generally straight configuration in an expanded deployed state that is substantially parallel to a longitudinal axis of a main vessel; and at least one stent coupled to the distal region of the graft, where the distal region of the graft includes a generally straight configuration in the expanded deployed state that is substantially parallel to a branch vessel, where a curvature of the central region varies an angle in which the distal region of the graft is disposed relative to the proximal region of the graft; and an expansion member coupled to the central region, where the expansion member comprises a resilient pre-formed material that promotes a curvature of the central region in the expanded deployed state.

18. The branch vessel prosthesis of claim 17 where an outer diameter at the proximal region of the graft is greater than an outer diameter at the distal region of the graft in the expanded deployed state.

19. The branch vessel prosthesis of claim 17, where a longitudinal length of the proximal region of the graft is greater than a longitudinal length of the distal region of the graft in the expanded deployed state.

20. The branch vessel prosthesis of claim 17, where the central region comprises at least one cross-sectional area that is greater than a cross-sectional area of each of the proximal and distal regions.

* * * * *